United States Patent
Utech et al.

(10) Patent No.: US 11,651,846 B2
(45) Date of Patent: *May 16, 2023

(54) MEDICATION DELIVERY MANAGEMENT

(71) Applicant: CareFusion 303, Inc., San Diego, CA (US)

(72) Inventors: Thomas William Utech, Dallas, TX (US); Maria Consolacion Jaskela, San Rafael, CA (US); William Lee Webster, Rockwall, TX (US)

(73) Assignee: CAREFUSION 303, INC., San Diego, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 17/204,859

(22) Filed: Mar. 17, 2021

(65) Prior Publication Data

US 2021/0202057 A1 Jul. 1, 2021

Related U.S. Application Data

(63) Continuation of application No. 16/538,710, filed on Aug. 12, 2019, now Pat. No. 10,971,259, which is a continuation of application No. 13/900,482, filed on May 22, 2013, now Pat. No. 10,380,326.

(51) Int. Cl.
*G16H 20/13* (2018.01)
*G16H 20/10* (2018.01)

(52) U.S. Cl.
CPC ............ *G16H 20/13* (2018.01); *G16H 20/10* (2018.01)

(58) Field of Classification Search
CPC .............................. G16H 20/13; G16H 20/10
See application file for complete search history.

(56) References Cited

U.S. PATENT DOCUMENTS

| | | | |
|---|---|---|---|
| 8,321,236 B2 | 11/2012 | Goodall et al. |
| 8,805,578 B2 | 8/2014 | Chudy |
| 2002/0198624 A1 | 12/2002 | Greenwald et al. |
| 2003/0018495 A1 | 1/2003 | Sussman |
| 2003/0098991 A1 | 5/2003 | Laverty |
| 2005/0096628 A1 | 5/2005 | Greeven et al. |
| 2005/0125097 A1 | 6/2005 | Chudy et al. |

(Continued)

FOREIGN PATENT DOCUMENTS

| | | |
|---|---|---|
| CN | 1890672 A | 1/2007 |
| CN | 101595438 A | 12/2009 |

(Continued)

OTHER PUBLICATIONS

Australian Office Action for Application No. 2020207772, dated Mar. 22, 2022, 5 pages.

(Continued)

*Primary Examiner* — Eliza A Lam
(74) *Attorney, Agent, or Firm* — Morgan, Lewis & Bockius LLP (57) ABSTRACT

The disclosed system identifies a preparation status of a first and second medication. Based on the delivery time and the completion time for the second medication, the system determines whether the first medication should be delivered prior to delivering the second medication and, when determining that the second medication should delivered prior to delivering the first medication, a notification to deliver the second medication before delivering the first medication is sent to a display device.

20 Claims, 6 Drawing Sheets

(56) References Cited

U.S. PATENT DOCUMENTS

| | | |
|---|---|---|
| 2006/0122729 A1 | 6/2006 | Murphy et al. |
| 2006/0178812 A1 | 8/2006 | Affleck et al. |
| 2006/0249423 A1 | 11/2006 | Reijonen |
| 2009/0012813 A1 | 1/2009 | Berzansky et al. |
| 2009/0043611 A1 | 2/2009 | Nadas et al. |
| 2010/0094653 A1 | 4/2010 | Tribble et al. |
| 2010/0161113 A1 | 6/2010 | Tribble et al. |
| 2010/0174552 A1 | 7/2010 | Hawkes et al. |
| 2012/0185277 A1 | 7/2012 | Tribble et al. |
| 2012/0205441 A1 | 8/2012 | Utech et al. |
| 2013/0018356 A1 | 1/2013 | Prince et al. |

FOREIGN PATENT DOCUMENTS

| | | |
|---|---|---|
| CN | 101706887 A | 5/2010 |
| CN | 101743548 A | 6/2010 |
| KR | 100738253 B1 | 7/2007 |

OTHER PUBLICATIONS

Australian Office Action for Application No. 2020207772, dated Nov. 25, 2021, 4 pages.

Chinese Office Action for Application No. 201480041367.6, dated Feb. 2, 2019, 9 pages.

Memo for Mexican Office Action for Application No. MX/a/2015/015955, memo dated Oct. 25, 2018, 4 pages.

Memo of Mexican Office Action for Application No. MX/A/2015/015955, dated Sep. 21, 2017, 3 pages.

Memo concerning Mexican Office Action for Application No. MX/a/2015/015955, memo dated Mar. 8, 2018, 3 pages.

Extended European Search Report and Written Opinion for Application No. 14800614.1, dated Jan. 5, 2017, 8 pages.

International Search Report and Written Opinion in PCT Patent Application No. PCT/US2014/039228 dated Aug. 22, 2014, 11 pages.

Australian Office Action for Application No. 2014268801, dated Jul. 19, 2019, 3 pages.

European Office Action for Application No. 14800614.1, dated Nov. 12, 2019, 6 pages.

India Office Action for Application No. 3845/KOLNP/2015, dated Dec. 19, 2019, 7 pages.

United Arab Emirates Office Action for Application No. UAE/P/1553/2015, first dated Nov. 21, 2019, 10 pages.

Australia Office Action for Application No. 2014268801, dated Feb. 11, 2020, 3 pages.

Brazil Office Action for Application No. BR112015028948-7, dated Feb. 12, 2020, 5 pages.

Australian Office Action for Application No. 2014268801, dated Jul. 6, 2020, 4 pages.

Canadian Office Action for Application No. 2912804, dated May 19, 2020, 5 pages.

Australia Office Action for Application No. 2014268801, dated Jul. 6, 2020, 4 pages.

Chinese Office Action for Application No. 202010066385.7, dated Jan. 19, 2021, 22 pages including machine translation.

Australian Decision Issued for Application No. 2014268801, dated Feb. 26, 2021, 21 pages.

Australian Office Action for Application No. 2020207772, dated Mar. 24, 2021, 4 pages.

MEDICATION DELIVERY MANAGEMENT

CROSS REFERENCE TO RELATED APPLICATIONS

This application is a continuation of U.S. application Ser. No. 16/538,710, entitled "MEDICATION DELIVERY MANAGEMENT," filed on Aug. 12, 2019, now U.S. Pat. No. 10,971,259, which is a continuation application of U.S. application Ser. No. 13/900,482, entitled "MEDICATION DELIVERY MANAGEMENT," filed on May 22, 2013, now U.S. Pat. No. 10,380,326, the entirety of each of which is incorporated herein by reference.

BACKGROUND

Field

The present disclosure generally relates to medication distribution, and, in particular, relates to systems and methods for managing delivery of a prepared medication in a healthcare facility.

Description of the Related Art

Certain pharmaceutical drugs are compounded to fit the needs of a patient. Compounding pharmacists combine or process appropriate ingredients using various tools to create a compounded pharmaceutical drug. For instance, compounding of sterile intravenous (IV) compounds can be done in anticipation of medication orders based on standard doses, or compounding can be done specific to a patient's need based on a physician order. Compounding may be done for medically necessary reasons, such as to change the form of the medication from a solid pill to a liquid, to avoid a non-essential ingredient that the patient is allergic to, or to obtain the exact dose(s) needed of particular active pharmaceutical ingredient(s). It may also be done for more optional reasons, such as adding flavors to a medication or otherwise altering taste or texture. Compounding is most routine in the case of intravenous (IV)/parenteral medication.

IV fluid delivery systems are used to deliver or "administer" such compounded IV medications (or "infusion solutions") in fluid form to patients at controlled rates. Many individuals suffer from acute and chronic health problems, the treatment of which could require regular, and sometimes extended, IV infusions. Certain treatment regimens for diseases such as infections, cancer and even basic fluid and electrolyte replacement, require the regular and sequenced infusion of precise amounts of intravenous medication for the patient's survival. Specifics of intravenous infusion of medications may depend on the patient, treatment regimen, and choices of the clinician and institution. Treating chronic medical disorders often requires the administration of medication over a long period of time according to a treatment regimen specified by a medical professional, such as a physician.

In cases of patients admitted to a healthcare facility, one or more infusions to be administered to a patient are prescribed by the patient's physician. A pharmacy, generally located within the patient's hospital or healthcare facility, prepares the infusion medication or solution according to the physician's prescription, for example, in a cleanroom (e.g., an environment having a controlled level of contamination that is specified by a number of particles per cubic meter at a specified particle size). An appropriately trained and credentialed pharmacist places the infusion solution in a bag, bottle, syringe, or other container and labels the container. The infusion solution is then commonly staged in a pickup location, such as a bin-sorting area. A sorting person is then responsible for placing each prepared infusion solution into bins or delivery carts that correspond to the locations where the infusion solutions will be delivered, such as an Intensive Care Unit (ICU). A delivery person retrieves the infusion solutions from the bins that correspond to areas of the healthcare facility to which that delivery person delivers. The delivery person then delivers the infusion solutions to the appropriate locations of the healthcare facility.

A delivery person may not have any knowledge whether an infusion solution that urgently needs to be delivered to an area of the hospital that the delivery person delivers to is sitting in the bin-sorting area, or is in the process of being prepared. Thus, even though there may be a prepared infusion solution sitting in the bin-sorting area that urgently needs to be delivered to an area of the healthcare facility that the delivery person delivers to, the delivery person may be unaware of the infusion solution and may leave without the infusion solution. Therefore another delivery person will need to be dispatched to urgently deliver the infusion solution.

The infusion solution is then delivered to the patient's location and a clinician such as a nurse or other clinician hangs the infusion solution from a rack. The nurse connects a tube between the infusion solution and an infusion pumping system and inserts a cannula at the end of the tube into the vessel of the patient for delivery of the infusion solution to the patient.

SUMMARY

According to certain embodiments of the present disclosure, a system for managing a delivery of prepared medications is provided. The system includes a memory that includes instructions, and one or more processors. The one or more processors are configured to execute the instructions to receive first information including a delivery deadline for a first medication, and receive second information including a preparation status of a second medication. The one or more processors are also configured to execute the instructions to compare the first information that includes the delivery deadline for the first medication with the second information that includes the preparation status of the second medication to determine whether the first medication should be indicated for delivery prior to completing preparation of the second medication, and provide a notification indicating when to deliver the first medication based on the determination.

According to certain embodiments of the present disclosure, a method for managing a delivery of prepared medications is provided. The method includes receiving first information including a delivery deadline for a first medication, and receiving second information including a preparation status of a second medication. The method also includes comparing the first information that includes the delivery deadline for the first medication with the second information that includes the preparation status of the second medication to determine whether the first medication should be indicated for delivery prior to completing preparation of the second medication, and providing a notification indicating when to deliver the first medication based on the determination.

According to certain embodiments of the present disclosure, a machine-readable storage medium that includes machine-readable instructions for causing a processor to execute a method for managing a delivery of prepared medications is provided. The method includes receiving first information including a delivery deadline for a first medication, and receiving second information including a preparation status of a second medication. The method also includes comparing the first information that includes the delivery deadline for the first medication with the second information that includes the preparation status of the second medication to determine whether the first medication should be indicated for delivery prior to completing preparation of the second medication, and providing a notification indicating when to deliver the first medication based on the determination.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

In the following detailed description, numerous specific details are set forth to provide a full understanding of the present disclosure. It will be apparent, however, to one ordinarily skilled in the art that the embodiments of the present disclosure may be practiced without some of these specific details. In other instances, well-known structures and techniques have not been shown in detail so as not to obscure the disclosure.

The disclosed system determines, upon a delivery person identifying (e.g., by scanning) a medication, such as an infusion solution, to be delivered, whether there are any other prepared or almost prepared medications that need to be delivered to the area of the hospital to which the delivery person is delivering the identified medication. If another medication is available or almost prepared for delivery, and it would be preferable to deliver the other medication during the same delivery as the identified medication, such as based on an urgency of the other medication or an expiration or delivery time of either medication, then a notification is provided to the delivery person to wait for the other medication to arrive for the appropriate bin prior to leaving to deliver the identified medication. The notification can be provided as an alert on a display of a device at or near the bin-sorting area, and/or may be sent to a device of the delivery person, such as the delivery person's mobile device. If another medication is available or almost prepared for delivery, but it is not preferable to deliver the other medication during the same delivery as the identified medication, then either no notification is provided to the delivery person, or a notification is provided to the delivery person to proceed with delivering the identified medication.

In this manner, the disclosed system provides the delivery person with insight into the medication preparation process by determining whether the delivery person should request (for delivery to the appropriate bin) a prepared medication that is sitting in the bin-sorting area from a sorting person, or whether the delivery person should wait for an medication to finish being prepared. The disclosed system may determine how urgently the medications identified (e.g., scanned) for delivery need to be delivered by the delivery person, and how long the delivery person will need to wait to obtain any other medication for which the preparation is almost complete. The disclosed system may notify (e.g., by a visible or audible alert, such as a text message or notification window) the delivery person of an medication that is almost prepared if the system determines that the delivery person has sufficient time to wait for the preparation of the medication to complete, e.g., based on an estimated amount of time required to complete the preparation of the medication, the times that the identified medications need to be delivered by, and an estimated amount of time required to deliver the identified medications.

Figure 1:
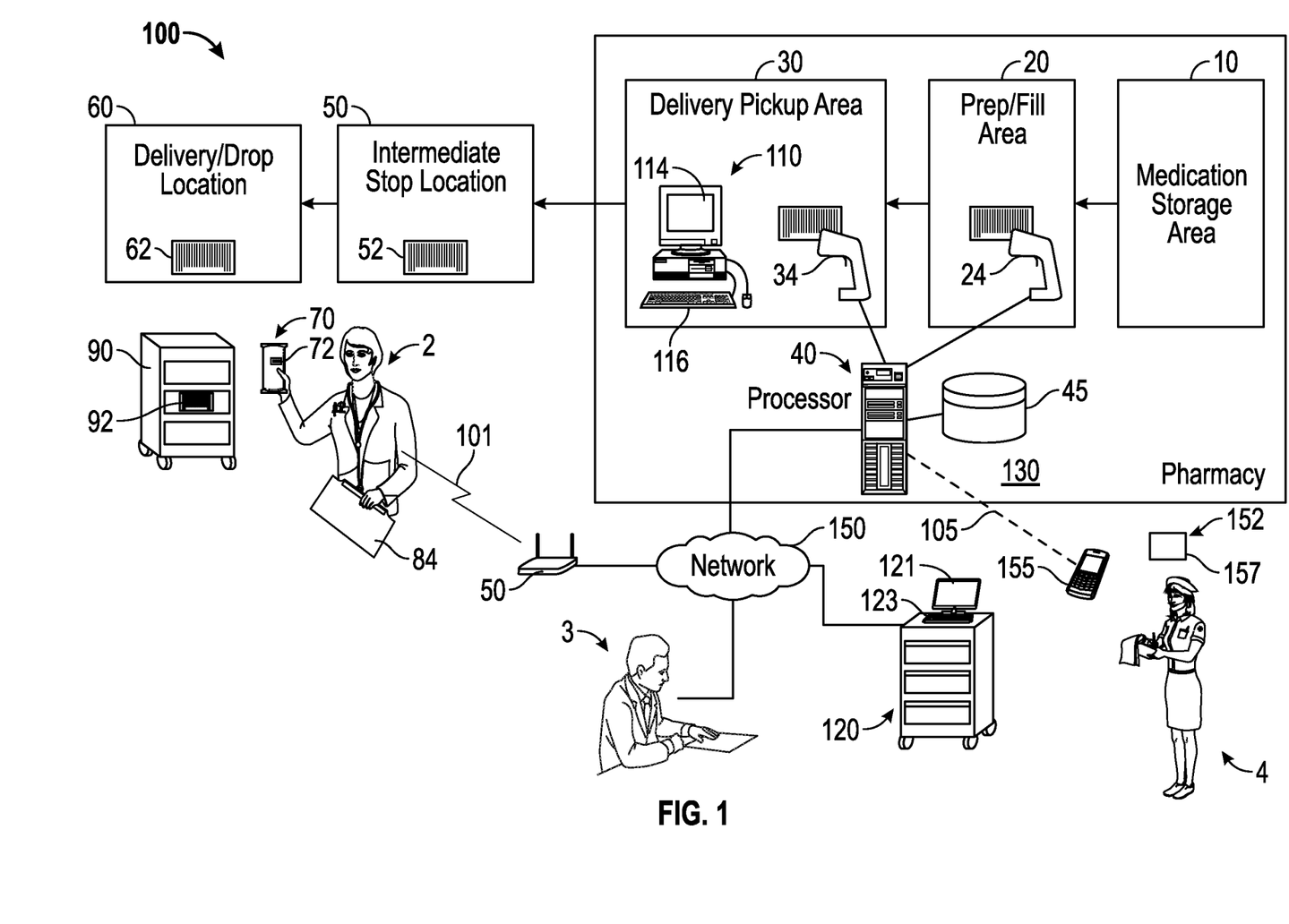
FIG. 1 illustrates an example architecture for managing a delivery of prepared medications.

FIG. 1 illustrates an example architecture 100 for managing a delivery of prepared medications according to certain aspects of the present disclosure. For ease and clarity of illustration only, without any intent to limit the scope of the present disclosure any way, it is assumed that the prepared medication provided as an example for FIG. 1 is an anesthetics IV solution.

The architecture 100 includes a pharmacy 1 having a medication storage area 10, a fill and/or preparation (fill/prep) area 20, and a delivery pickup area 30 (e.g., bin-sorting area). The medication storage area 10 includes a plurality of medications and supplies including an anesthetic drug (e.g., bupivicanine or chloroprocaine) and an appropriate fluid for the anesthetic drug. The anesthetic drug and the fluid are taken from the medication storage area 10 to the prep/fill area 20 where they are mixed together to produce the anesthetics IV solution. A patient/medication ID device 72, such as a barcode label or an radio frequency identification (RFID) tag, is provided on (e.g., affixed to) a package 70 (e.g., IV bag) containing the IV solution at the prep/fill area 20. The patient/medication ID device 72 includes patient/medication ID information indicative of the medication and the patient to whom the medication is prescribed. The package 70 is then taken by a technician at the pharmacy 1 to the delivery pickup area 30. The technician determines an appropriate bin or delivery cart 90 into which to place the package 70, and then loads the package 70 onto the appropriate delivery cart 90 for delivery to a scheduled delivery/drop location 60 (e.g., a patient room) by a delivery person 2.

In the illustrated embodiment, the prep/fill area 20 has a barcode reader 24 provided therein that the technician at the pharmacy 1 can use to read the patient/medication ID device 72 (a barcode label in the illustrated example) before the package 70 is taken to the delivery pickup area 30. The delivery pickup area 30 has a barcode reader 34 connected to a client 110 provided therein that the technician at the pharmacy 1 can use to read the patient/medication ID device 72 once the package 70 is taken to the delivery pickup area 30. The delivery cart 90 may also be provided with a location barcode label reader. The delivery person 2 can use the barcode reader 34 to scan the package 70 to indicate the delivery person 2 will begin delivery of the package 70.

The pharmacy 1 includes a server 130 (e.g., pharmacy server) that includes a processor 40. The server 130 can be any device having an appropriate processor, memory, and communications capability for receiving, processing, and sending information associated with a medication database 45. The processor 40 is coupled to the medication database 45 that is configured to store a variety of information including order status information and delivery progress information to be discussed below. The processor 40 is configured to receive an order for the medication from a doctor 3, and to determine whether to notify the delivery person 2 to begin delivery of the package 70 or wait for preparation of another package to be completed (e.g., based on the order) prior to delivery of the package 70. For example, a notification can be sent to a client 110 for display on an output device 114 at or near the delivery pickup area 30 instructing the delivery person 2 to hold delivery of the package 70 until the other package is prepared, and optionally confirm receipt of the notification using an input device 116 of the client 110. The client 110 can be, for example, a computer system associated with the delivery pickup area 30 such as a desktop computer or mobile computer. The client 110 can also be, for example, a tablet computer, mobile device (e.g., a smartphone or PDA), or any other device having appropriate processor, memory, and communications capabilities. The mobile device may, for example, be associated with the delivery person 2.

Also depicted in FIG. 1 is an intermediate stop location 50 (e.g., a first patient room), located between the pharmacy 1 and the delivery location 50. The delivery cart 90 may make a temporary stop at the intermediate stop location 50, e.g., for delivering another package containing a medication for the patient in the first patient room.

The delivery location 60 and/or the intermediate stop location 50 can include, for example, patient rooms having an infusion device for providing an IV infusion from a package to a patient. In the illustrated example, the intermediate stop location 50 and the delivery location 60 are provided with location barcode label 52 and location barcode label 62, respectively. Each of the location barcode labels 52, 62 includes a unique location ID information indicative of the respective location 50, 60 where the corresponding barcode label is provided. As described above, the package 70 (e.g., IV bag) containing the medication (e.g., IV solution) is provided with a patient/medication identification (ID) device 72. In the illustrated example, the patient/medication ID device 72 is a barcode label that includes patient/medication information indicative of the patient (e.g., "Jane Smith") and the medication (e.g., "bupivicanine IV solution"). The patient/medication information may also contain other drug or patient related information such as the patient's medical conditions (e.g., allergies), name of the drug (e.g., bupivicanine), the drug dosage, the drug concentration, the drug administration schedules, and the drug administration rate.

Also depicted in the architecture 100 of FIG. 1 is a reader device 84 that is hand carried by the delivery person 2 and/or attached to the delivery cart 90 and is configured to read the patient/medication information from the patient/medication ID device 72 provided on the package 70. In the illustrated example, the reader device 84 is a barcode scanner. In those embodiments in which the barcode scanner 84 is hand carried by the delivery person 2, the scanner 84 is also configured to read the location ID information from the location barcode labels 52, 62, 92.

In the embodiments described above, the location ID devices 52, 62, 92 and/or the patient/medication ID device 72 are passive ID devices, meaning that certain action (e.g., scanning) has to be taken by the participant (e.g., a pharmacy technician or the delivery person 2) to retrieve information therefrom. In other embodiments, the ID devices can be active ID devices, meaning that the information retrieval from the ID devices occur automatically without an action taken by the participant. In some embodiments, the active ID devices can actively transmit signals containing the relevant information to the reader device 72 through a wireless link. The wireless link can use a variety of technologies including Bluetooth, ZigBee, wireless USB, and proprietary systems. In other embodiments, the active ID devices do not themselves transmit signals, but respond to query signals generated by a reader device (e.g., by altering impedance of an RF circuit therein) as the reader device passes by the ID devices in close proximity.

In the illustrated example, each time the barcode scanner 84 scans an ID device (e.g., patient/medication ID device or location ID device), the information read thereby is wirelessly transmitted to a wireless bridge 50 that receives the information. The bridge 50 is in data communication with the processor 40 via a hospital network 150. The network 150 can include, for example, any one or more of a personal area network (PAN), a local area network (LAN), a campus area network (CAN), a metropolitan area network (MAN), a wide area network (WAN), a broadband network (BBN), the Internet, and the like. Further, the network 150 can include, but is not limited to, any one or more of the following network topologies, including a bus network, a star network, a ring network, a mesh network, a star-bus network, tree or hierarchical network, and the like.

The processor 40 is configured to receive medication/patient ID information and/or location ID information read by the barcode scanner 84, generate delivery progress information therefrom, and store the delivery progress information in the medication database 45. The medication database 45 can include information such as, but not limited to: the patient's name or ID; the medication name or ID, the scheduled delivery location 60, the scheduled delivery time, an expiration date or time for a prepared medication, an urgency of delivery of the prepared medication, one or more read locations where the medication/patient ID information and/or the location ID information was read by the barcode scanner 84, time when the information was read, and the name or ID of the delivery person 2.

The architecture 100 further comprises tracking devices 120, 152 that allow a care provider 4 (e.g., a nurse assigned the task of administering the patient-specific medication to the patient) to monitor the progress of the delivery of the medication. Each of the tracking devices 120, 152 is configured to receive a tracking request by the care provider 4, access the medication database 45, either directly or via the processor 40, retrieve the delivery progress information stored in the database 45, and indicate a delivery progress of the medication to the care provider 4 based on the delivery progress information. In the illustrated example, the tracking device 120 is an automated dispensing machine having a processor (not shown), a display 121, and a keyboard 123; and the tracking device 152 is a mobile communication device (e.g., a cell phone, personal digital assistant (PDA), or pager) having a processor (not shown), a display 151, and a keyboard 153. The delivery progress information can inform the care provider 4 of a last-known read location and time of the last reading. Based on such information, the care provider 4 can decide, e.g., whether to wait for the delivery at the delivery location 60, go to the delivery location later at an expected delivery time, or go to the last-known location to retrieve the medication from the cart 90.

Figure 2:
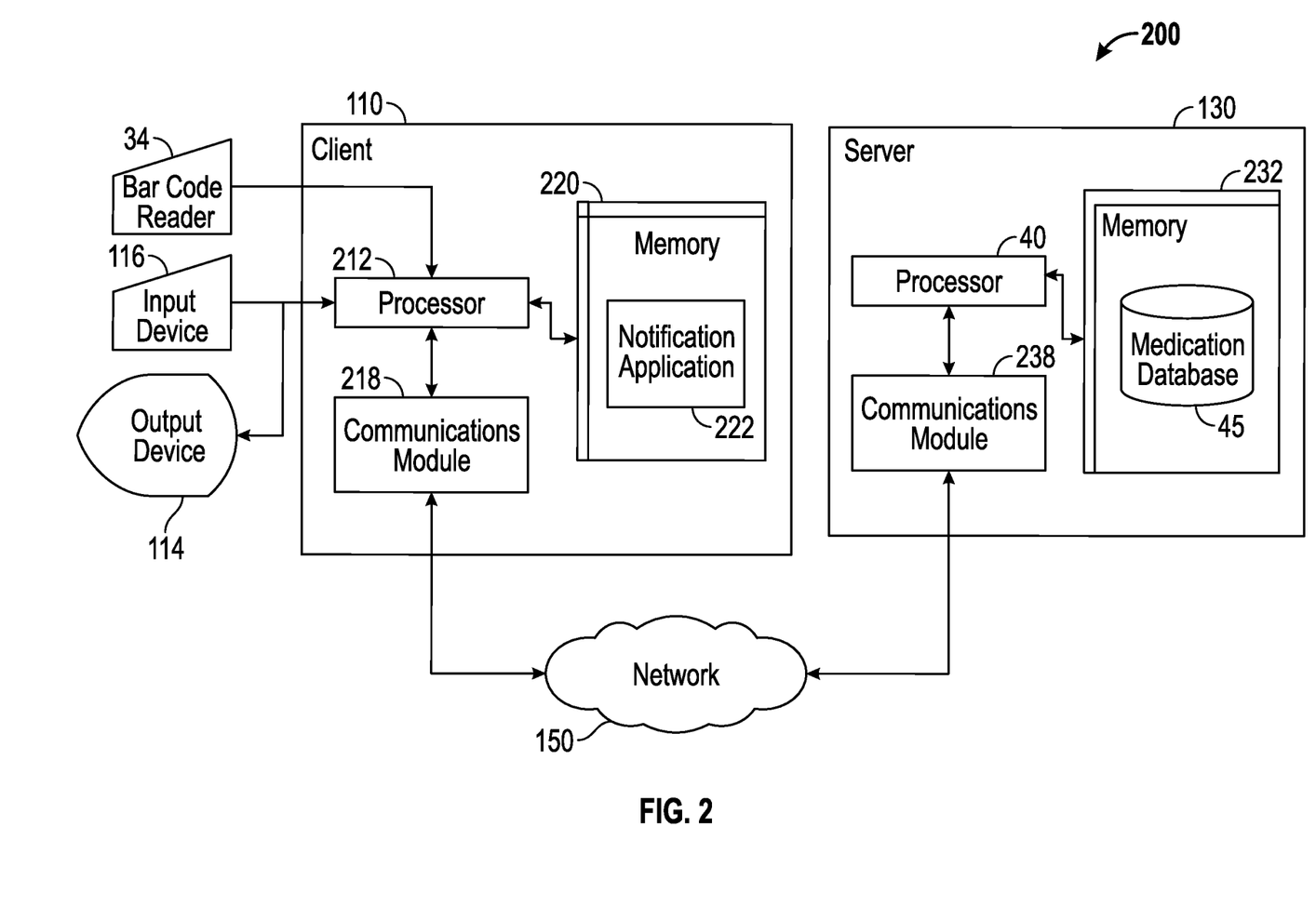
FIG. 2 is a block diagram illustrating the example client and server from the architecture of FIG. 1 according to certain aspects of the disclosure.

FIG. 2 is a block diagram 200 illustrating an example server 130 and client 110 in the architecture 100 of FIG. 1 according to certain aspects of the disclosure. The client 110 and the server 130 are connected over the network 150 via respective communications modules 218 and 238. The communications modules 218 and 238 are configured to interface with the network 150 to send and receive information, such as data, requests, responses, and commands to other devices on the network 150. The communications modules 218 and 238 can be, for example, modems or Ethernet cards.

The server 130 includes a processor 40, a communications module 238, and a memory 232 that includes the medication database 45. The processor 40 of the server 130 is configured to execute instructions, such as instructions physically coded into the processor 40, instructions received from software in memory 240, or a combination of both. For example, the processor 40 of the server 130 executes instructions to receive first information including a delivery deadline for a first medication (e.g., package 70) and receive second information including a preparation status of a second medication. For instance, when the delivery person 2 uses the barcode reader 34 of the client 110 to scan the package 70 at the delivery pickup area 30, the processor 212 of the client 110 sends information identifying the package 70 via a communications module 218 over the network 150 to the server 130. The processor 40 of the server 130 may then query the medication database 45 to determine a delivery deadline for the first medication and a delivery location for the first medication.

The processor 40 may also query the medication database 45 to receive information indicating the preparation status of a second medication. The preparation status of the second medication can include, for example, a status indicating that the second medication is ready but not yet sorted into a bin in the delivery pickup area 30, a current location of the second medication, an indication that preparation of the second medication is almost complete, or an estimated amount of time to finish preparation of the second medication. The received information can also include a delivery location for the second medication.

The processor 40 of the server 130 compares the first information including the delivery deadline for the first medication with the second information including the preparation status of the second medication to determine whether the first medication should be indicated for delivery prior to completing preparation of the second medication. The completed preparation of the second medication includes, in certain aspects, delivery of the second medication to the delivery pickup area 30. The determination can be based on various factors including, for instance, a degree of urgency for delivery of the first medication or the second medication, the delivery deadline for the first medication, the preparation status of the second medication, an estimated amount of time remaining for the completing preparation of the second medication, the intended delivery location of the first medication or the second medication, or an estimated amount of time required to deliver either the first medication or the second medication.

The processor 40 provides a notification (e.g., to the client 110) indicating when to deliver the first medication based on the determination. The notification can be provided, for example, as a computer generated alert for display on a screen, or as a text message. The notification can, for example, indicate that the delivery person 2 should wait for the preparation of the second medication to be completed prior to delivering the first medication to the delivery/drop location 60. This may be the case where, for example, the second medication is indicated as being needed urgently and requiring delivery within a short time period and the first medication is not indicated as being needed urgently. As another example, the notification can indicate that the delivery person 2 should wait for the preparation of the second medication to be completed prior to delivering the first medication to the delivery/drop location 60 because the delivery location for the first medication, delivery/drop location 60, is at or near the delivery location for the second medication, intermediate stop location 50.

Alternatively, the notification provided by the processor 40 of the server 130 can indicate that the delivery person 2 should not wait for the preparation of the second medication to be completed prior to delivering the first medication to the delivery/drop location 60, but instead proceed with delivering the first medication to the delivery/drop location 60. This may be the case where, for example, the estimated time to prepare the second medication would exceed the delivery deadline of the first medication.

The notification is provided by the processor 40 to the client 110. A notification application 222 in the memory 220 of the client 110 may receive the notification and, for example, provide an audible or visible alert using the output device 114. For example, the client 110 can be a mobile device of the delivery person 2, and the notification can be a text message sent to the mobile device for display. As another example, the client 110 can be a computer located at the delivery pickup area 30 and the notification can be a visual alert displayed on the output device 114 of the computer. When the preparation status of the second medication indicates the second medication has been prepared but is not yet sorted for the appropriate delivery bin at the delivery pickup area 30, the visual alert can include an interface for the delivery person 2 to request that the prepared second medication be delivered (e.g., by a pharmacy technician) to the appropriate delivery bin at the delivery pickup area 30. The delivery person 2 may use the input device 116 of the client 110 to confirm the request to deliver the prepared second medication to the delivery pickup area 30. The visual alert can also identify a degree of urgency for delivery of either the first medication or the second medication.

Figure 3:
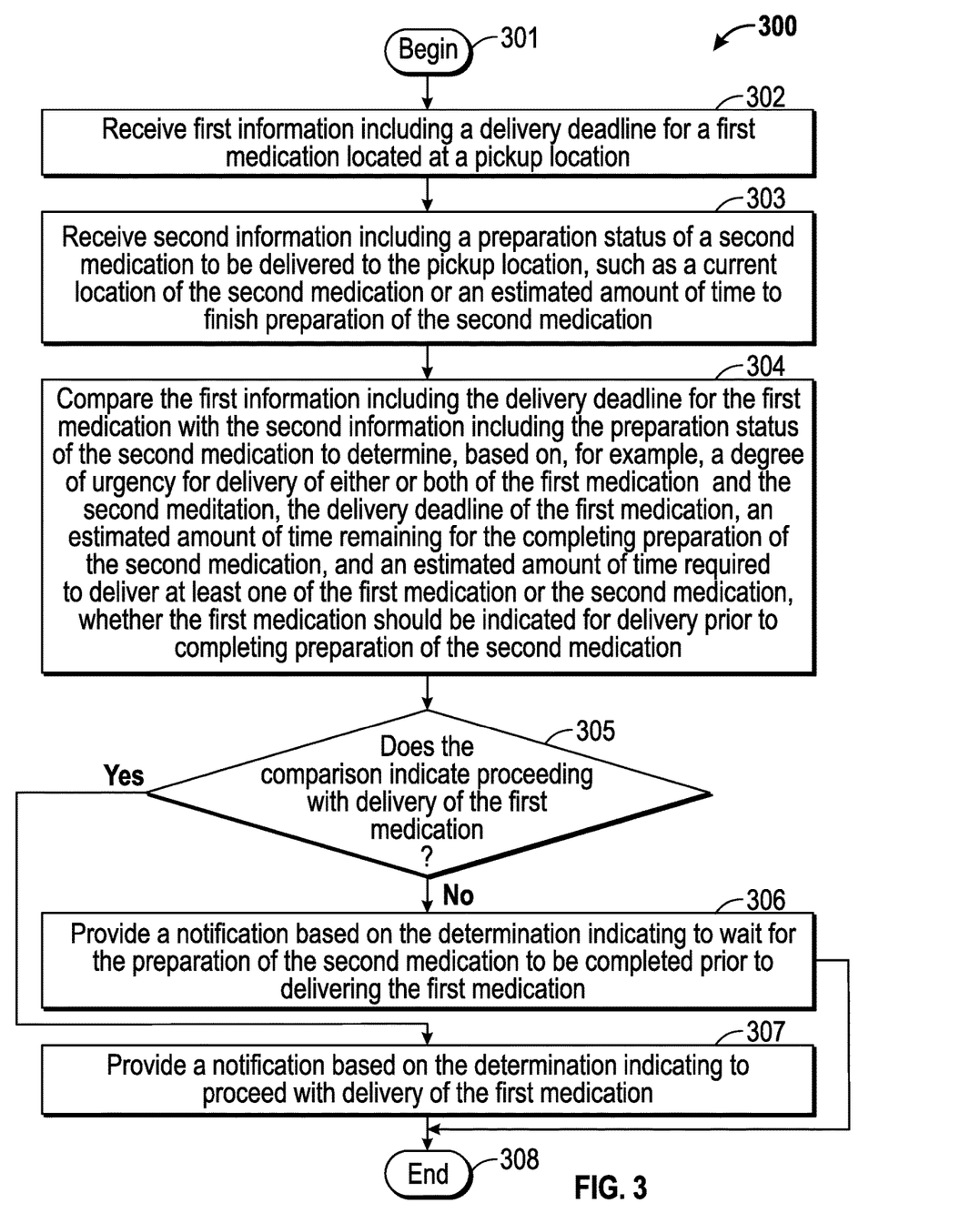
FIG. 3 illustrates an example process for managing a delivery of prepared medications using the server of FIG. 2.

FIG. 3 illustrates an example process 300 for managing a delivery of prepared medications using the server 130 of FIG. 2. While FIG. 3 is described with reference to FIG. 2, it should be noted that the process steps of FIG. 3 may be performed by other systems.

The process 300 begins by proceeding from beginning step 301 when a first medication, such as the package 70, is identified (e.g., scanned by a barcode reader 34 of the client 110) at a delivery pickup area 30, such as by a delivery person 2, to step 302 when the server 130 (e.g., at the pharmacy 1) receives first information including a delivery deadline for the first medication located at the delivery pickup area 30. Next, in step 303, the server 130 receives second information (e.g., from the medication database 45 in memory 232) including a preparation status of a second medication to be delivered to the delivery pickup area 30, such as a current location of the second medication or an estimated amount of time to finish preparation of the second medication. In step 304, the first information including the delivery deadline for the first medication is compared with the second information including the preparation status of the second medication to determine whether the first medication should be indicated for delivery prior to completing preparation of the second medication. The determination may be based on any of, for example, a degree of urgency for delivery of either or both of the first medication and the second medication, the delivery deadline of the first medication, an estimated amount of time remaining for the completing preparation of the second medication, and an estimated amount of time required to deliver at least one of the first medication or the second medication.

If the comparison of step 304 does not indicate proceeding with delivery of the first medication, then the process 300 proceeds to step 306 in which a notification based on the determination is provided (e.g., to the client 110) indicating to wait for the preparation of the second medication to be completed prior to delivering the first medication. If, however, the comparison of step 304 indicates proceeding with delivery of the first medication, then the process 300 proceeds to step 307 in which a notification based on the determination is provided (e.g., to the client 110) indicating to proceed with delivery of the first medication. The process 300 then ends in step 308.

FIG. 3 sets forth an example process 300 for managing a delivery of prepared medications using the server 130 of FIG. 2. Examples will now be described using the example process 300 of FIG. 3 and various medications for delivery at different stages in the preparation process.

In one example where a delivery person 2 is instructed to wait for preparation of a second medication to be completed, the process 300 begins by proceeding from beginning step 301 when the delivery person 2 scans a first medication, Vancomycin, using a barcode reader 34 of the client 110, which is a computer terminal, at the delivery pickup area 30. Next, in step 302, the server 130 at the pharmacy 1 receives first information identifying the scanned Vancomycin and a delivery deadline for the scanned Vancomycin. Next, in step 303, the server 130 receives second information from the medication database 45 in memory 232 that includes a preparation status of two other medications, Cefazolin (1 gm/NS 50 ml) and Cefazolin (2 gm/NS 50 ml), that are intended to be delivered to the delivery pickup area 30. The preparation status indicates that the two other medications are identified as high priority (e.g., photostat or "stat"), are currently being prepared in the fill/prep area 20, and based on how much of the preparation has been completed, an estimated amount of time to finish preparation of the other medications.

In step 304, the delivery deadline for the scanned Vancomycin is compared with the priority of the other medications, their location, their delivery deadlines, their delivery location, an estimated amount of time required to deliver at least one of the first medication or the second medication, and an amount of time estimated for preparation of the other medications to be completed, to determine whether the delivery person 2 should wait for preparation of Cefazolin (1 gm/NS 50 ml) and Cefazolin (2 gm/NS 50 ml) to be completed prior to leaving to deliver the Vancomycin at the delivery/drop location 60. The comparison of step 304 indicates in step 305 to wait for the preparation of Cefazolin (1 gm/NS 50 ml) and Cefazolin (2 gm/NS 50 ml) to be completed and delivered to the delivery pickup area 30 because of their high priority, their nearness to completion, their close delivery deadlines, and the proximity of their delivery location at intermediate stop location 50 to the delivery/drop location 60 for the scanned Vancomycin.

Figure 4A:
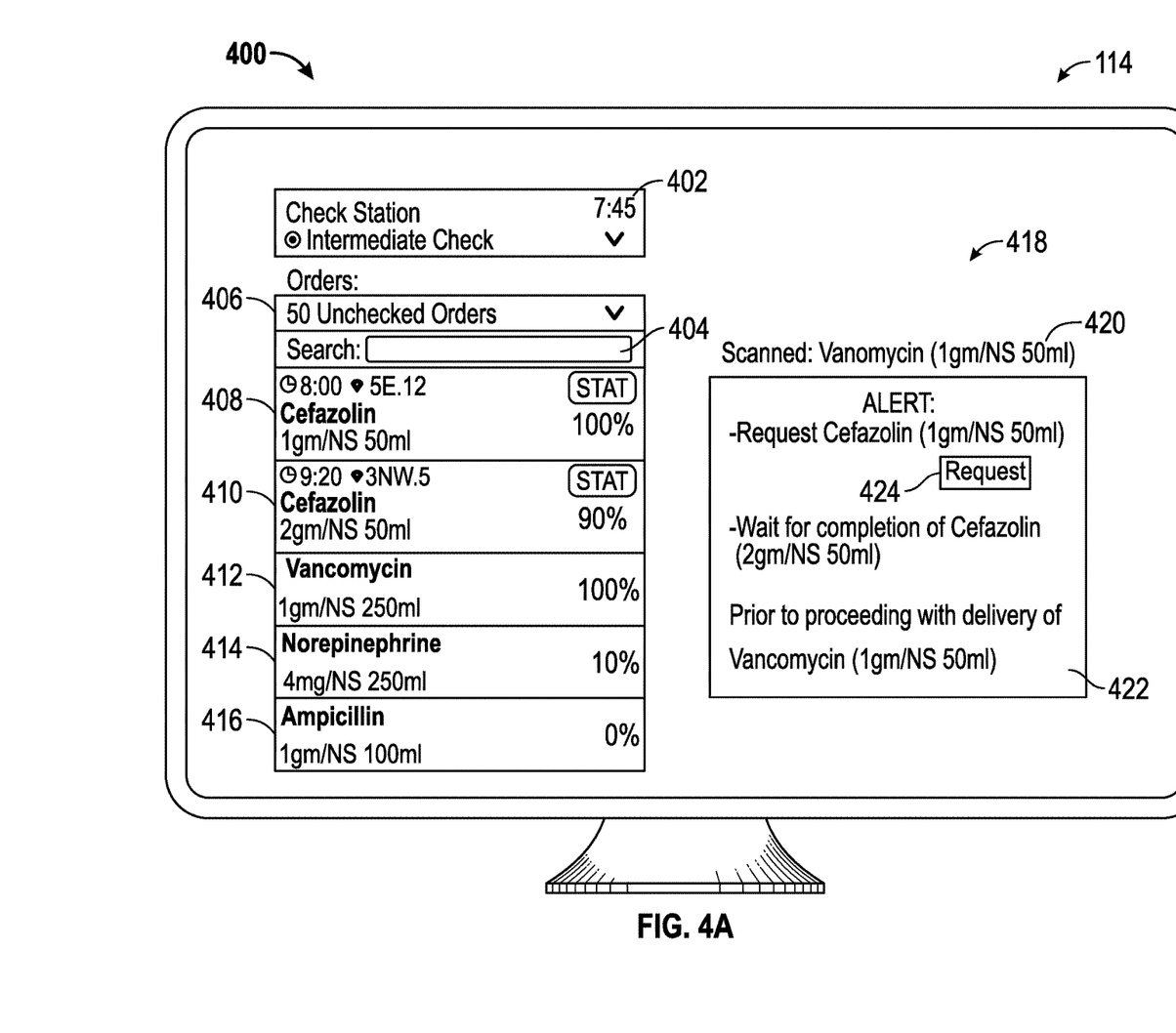
FIGS. 4A and 4B are example illustrations associated with the example process of FIG. 3.

In step 306, the server 130 sends a notification to the computer terminal 110 for display to the delivery person 2 as provided in the example illustration 400 of FIG. 4A. The example illustration is of the output device 114, a display screen, of the computer terminal 110. The display includes a user interface identifying a current time 402, and a list of 50 unchecked orders 406 that may be sorted by, for example, priority, due time, location, or alphabetically and may be searched using a search interface 404. Five orders 408, 410, 412, 414, and 416 are listed and additional orders may be viewed by scrolling the interface below the five listed orders 408, 410, 412, 414, and 416. For each order, a due time, patient location, medication information, preparation status, and level of priority may be indicated. For example, the first order 408 listed identifies the medication as Cefazolin (1 gm/NS 5 ml), a high priority "stat" medication whose preparation status is 100% (i.e., completely prepared) and due by 8:00 AM to patient location 5E-12.

The user interface also includes a messages area 418 that both identifies 420 the medication scanned by the delivery person 2, namely the third listed order 412 of Vancomycin (1 gm/NS 50 ml), and provides the notification 422 (of step 306) for the delivery person 2 to read. The notification 422 indicates to the delivery person 2 to request, using a "request" button 424, that the first listed order 408, Cefazolin (1 gm/NS 50 ml), be sorted into the appropriate bin in the delivery pickup area 30, prior to proceeding with delivery of the scanned Vancomycin. The notification 422 also indicates to the delivery person 2 to wait for completion of the second listed order 410, Cefazolin (2 gm/NS 50 ml). The process 300 then ends in step 308.

In another example where a delivery person 2 is instructed to proceed with delivery of a first medication prior to completion of preparation of a second medication, the process 300 begins by proceeding from beginning step 301 when the delivery person 2 scans two medications, Vancomycin and Norepinephrine, using a barcode reader 34 of the client 110, which is a handheld display and scanner (e.g., such as reader device 84), at the delivery pickup area 30. Next, in step 302, the server 130 at the pharmacy 1 receives first information identifying the scanned Vancomycin and Norepinephrine and a delivery deadline for the scanned Vancomycin and Norepinephrine. Next, in step 303, the server 130 receives second information from the medication database 45 in memory 232 that includes a preparation status of two other medications, Cefazolin (1 gm/NS 50 ml) and Cefazolin (2 gm/NS 50 ml), that are intended to be delivered to the delivery pickup area 30. The preparation status indicates that the two other medications are identified as high priority, are currently being prepared in the fill/prep area 20, and based on how much of the preparation has been completed, an estimated amount of time to finish preparation of the other medications.

In step 304, the delivery deadlines for the scanned Vancomycin and Norepinephrine are compared with the priority of the other medications, their location, their delivery deadlines, their delivery location, an estimated amount of time required to deliver at least one of the first medication or the second medication, and an amount of time estimated for preparation of the other medications to be completed, to determine whether the delivery person 2 should wait for preparation of Cefazolin (1 gm/NS 50 ml) and Cefazolin (2 gm/NS 50 ml) to be completed prior to leaving to deliver the Vancomycin and Norepinephrine at the delivery/drop location 60. The comparison of step 304 indicates in step 305 to proceed with delivery of the Vancomycin and Norepinephrine because, for example, preparation of the Cefazolin (1 gm/NS 50 ml) and Cefazolin (2 gm/NS 50 ml) is only 10% completed and their deadline for delivery is not near.

Figure 4B:
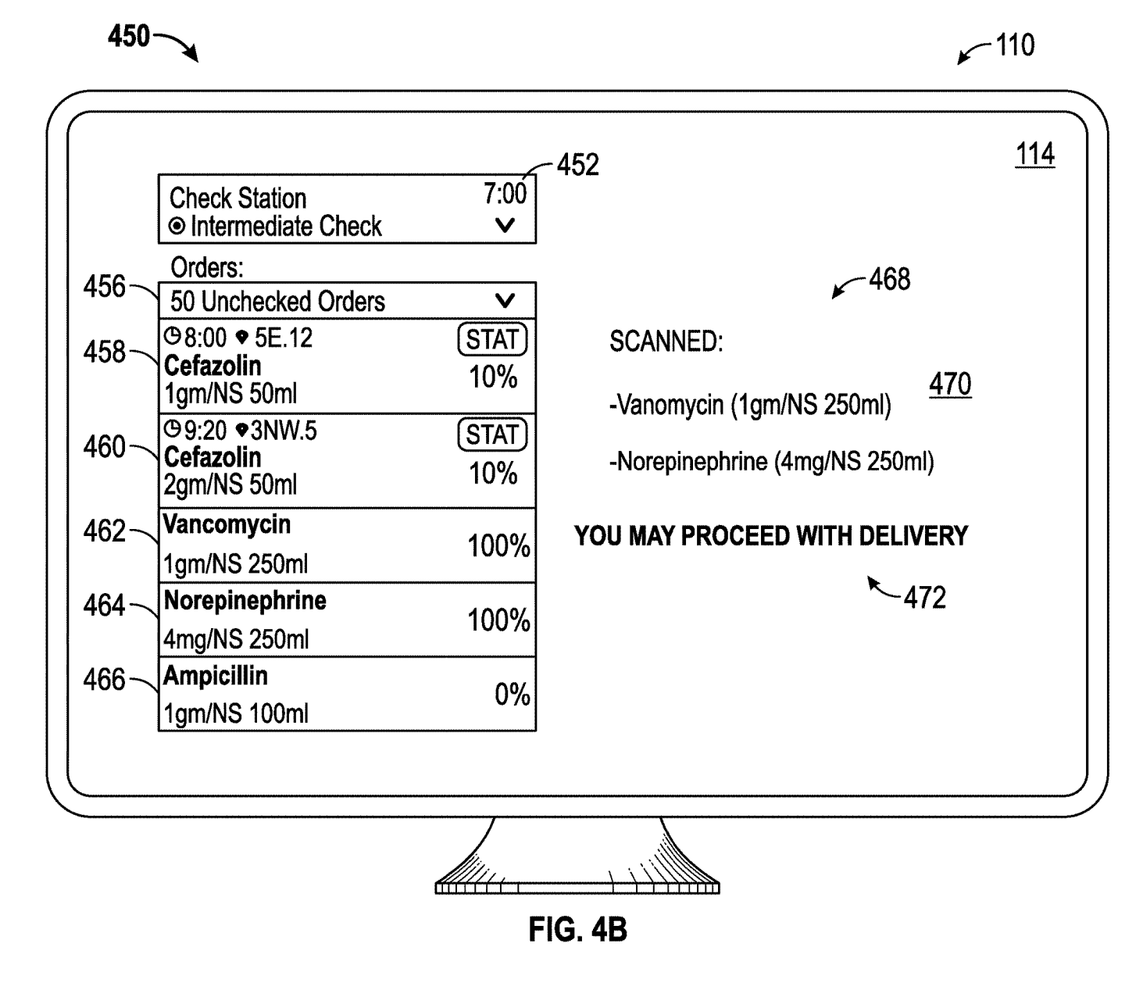

In step 306, the server 130 sends a notification to the handheld device 110 for display to the delivery person 2 as provided in the example illustration 450 of FIG. 4B. The example illustration is of the output device 114, a display screen, of the handheld device 110. The display includes a user interface identifying a current time 452, and a list of 50 unchecked orders 456. Five orders 458, 460, 462, 464, and 466 are listed and additional orders may be viewed by scrolling the interface below the five listed orders 458, 460, 462, 464, and 466. For each order, a due time, patient location, medication information, preparation status, and level of priority may be indicated. For example, the first order 458 listed identifies the medication as Cefazolin (1 gm/NS 5 ml), a high priority "stat" medication whose preparation status is 10% complete and due by 8:00 AM to patient location 5E-12.

The user interface also includes a messages area 468 that both identifies 470 the medications scanned by the delivery person 2, and provides the notification 472 (of step 306) for the delivery person 2 to read. The notification 472 indicates to the delivery person 2 to proceed with delivery of the scanned Vancomycin and Norepinephrine. The process 300 then ends in step 308.

Figure 5:
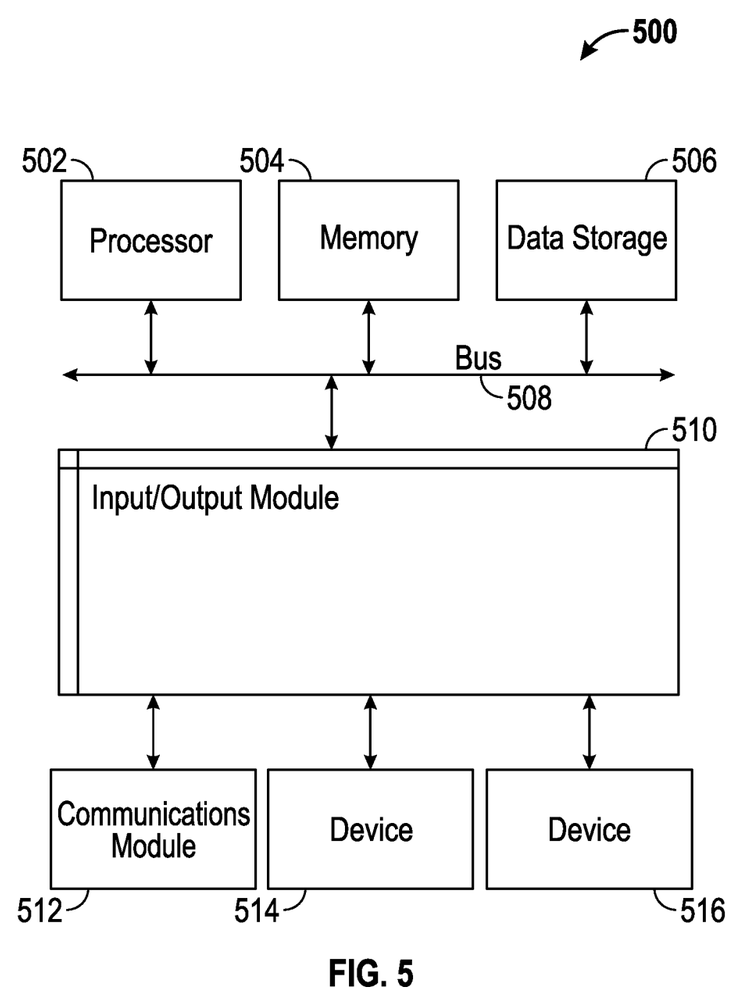
FIG. 5 is a block diagram illustrating an example computer system with which the client and server of FIG. 2 can be implemented.

FIG. 5 is a block diagram illustrating an example computer system 500 with which the client 110 and server 130 of FIG. 2 can be implemented. In certain aspects, the computer system 500 may be implemented using hardware or a combination of software and hardware, either in a dedicated server, or integrated into another entity, or distributed across multiple entities.

Computer system 500 (e.g., client 110 and server 130) includes a bus 508 or other communication mechanism for communicating information, and a processor 502 (e.g., processor 212 and 40) coupled with bus 508 for processing information. By way of example, the computer system 500 may be implemented with one or more processors 502. Processor 502 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information.

Computer system 500 can include, in addition to hardware, code that creates an execution environment for the computer program in question, e.g., code that constitutes processor firmware, a protocol stack, a database management system, an operating system, or a combination of one or more of them stored in an included memory 504 (e.g., memory 220 and 232), such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 508 for storing information and instructions to be executed by processor 502. The processor 502 and the memory 504 can be supplemented by, or incorporated in, special purpose logic circuitry.

The instructions may be stored in the memory 504 and implemented in one or more computer program products, i.e., one or more modules of computer program instructions encoded on a computer readable medium for execution by, or to control the operation of, the computer system 500, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, embeddable languages, and xml-based languages. Memory 504 may also be used for storing temporary variable or other intermediate information during execution of instructions to be executed by processor 502.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 500 further includes a data storage device 506 such as a magnetic disk or optical disk, coupled to bus 508 for storing information and instructions. Computer system 500 may be coupled via input/output module 510 to various devices (e.g., barcode reader 34). The input/output module 510 can be any input/output module. Example input/output modules 510 include data ports such as USB ports. The input/output module 510 is configured to connect to a communications module 512. Example communications modules 512 (e.g., communications module 218 and 238) include networking interface cards, such as Ethernet cards and modems. In certain aspects, the input/output module 510 is configured to connect to a plurality of devices, such as an input device 514 (e.g., input device 116) and/or an output device 516 (e.g., output device 114). Example input devices 514 include a keyboard and a pointing device, e.g., a mouse or a trackball, by which a user can provide input to the computer system 500. Other kinds of input devices 514 can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 516 include display devices, such as a LED (light emitting diode), CRT (cathode ray tube), or LCD (liquid crystal display) screen, for displaying information to the user.

According to one aspect of the present disclosure, the client 110 and server 130 can be implemented using a computer system 500 in response to processor 502 executing one or more sequences of one or more instructions contained in memory 504. Such instructions may be read into memory 504 from another machine-readable medium, such as data storage device 506. Execution of the sequences of instructions contained in main memory 504 causes processor 502 to perform the process steps described herein. One or more processors in a multi-processing arrangement may also be employed to execute the sequences of instructions contained in memory 504. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network (e.g., network 150) can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 500 can include clients and servers. A client and server are generally remote from each other and typically interact through a communication network. The relationship of client and server arises by virtue of computer programs running on the respective computers and having a client-server relationship to each other. Computer system 500 can be, for example, and without limitation, a desktop computer, laptop computer, or tablet computer. Computer system 500 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 502 for execution. Such a medium may take many forms, including, but not limited to, non-volatile media, volatile media, and transmission media. Non-volatile media include, for example, optical disks, magnetic disks, or flash memory, such as data storage device 506. Volatile media include dynamic memory, such as memory 504. Transmission media include coaxial cables, copper wire, and fiber optics, including the wires that comprise bus 508. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other variations are within the scope of the following claims.

These and other implementations are within the scope of the following claims.

What is claimed is:

1. A system for managing a delivery of prepared medications, the system comprising:
    one or more processors; and
    a machine-readable memory having instructions stored thereon that, when executed by the one or more processors, cause a computing device to perform operations comprising:
        receiving an identification of a first medication indicated for delivery to a first location within a healthcare facility, the identification of the first medication being received from a reader device and including information obtained from an active identification device affixed to a container of the first medication, the active identification device configured to automatically transmit the information wirelessly to the reader device when within a proximity of the reader device without a further action taken by a participant;
        identifying a preparation status of a second medication designated for delivery to a second location within the healthcare facility;
        determining delivery times and priorities for the first medication and the second medication, and a completion time for the second medication;
        determining, based on the delivery times and priorities for the first medication and the second medication and the completion time for the second medication, whether the second medication should be delivered prior to delivering the first medication; and
        providing, for display at a display device, when determining that the second medication should be delivered prior to delivering the first medication, a notification indicating the second medication should be delivered before delivering the first medication.

2. The system of claim 1, wherein the operations further comprise:
    determining that the first medication should not be delivered prior to completing a preparation of the second medication;
    providing, a notification to wait for the preparation of the second medication before delivering the first medication;
    providing a prompt to request that the second medication be provided to a delivery pickup area for delivery prior to the delivery of the first medication; and
    receiving, prior to the delivery of the first medication, from the display device, confirmation that the second medication was provided to the delivery pickup area for delivery to the second location prior to the delivery of the first medication to the first location.

3. The system of claim 2, wherein the operations further comprise:
    receiving, based on a scanning of a container of the first medication, a second indication that a delivery person has received the first medication at the delivery pickup area for delivery to the first location;
    wherein determining whether the second medication should be delivered prior to delivering the first medication is performed responsive to receiving the second indication.

4. The system of claim 1, wherein the operations further comprise:
    determining that the second medication is a high priority medication, wherein determining that the first medication should not be delivered prior to delivering the second medication is based on the second medication being determined to be the high priority medication.

5. The system of claim 1, wherein the operations further comprise:
    receiving, based on a scanning of a container of the second medication, progress information regarding the delivery of the second medication to the second location;
    receiving a request to retrieve the progress information from a user;
    providing, responsive to the request, the progress information together with a last-known location of the second medication.

6. The system of claim 5, wherein the last-known location is not the second location.

7. The system of claim 1, wherein the operations further comprise:
    providing, for display at the display device, a user interface comprising a prioritized list of medication orders, a first order in the prioritized list comprising the first medication, wherein the operations further comprise:
    selectively reordering the prioritized list of the user interface to display a second order for the second medication over the first order based on respective priorities associated with each of the medication orders in the prioritized list, respective due times associated with each of the medication orders, and respective patient locations associated with each of the medication orders.

8. The system of claim 1, wherein a preparation of the first medication is completed before a preparation of the second medication, the operations further comprising:
    determining an expiration time of the first medication or the second medication, wherein determining that the second medication should be delivered prior to delivering the first medication is further based on the expiration time of the first medication or the second medication.

9. The system of claim 8, wherein the operations further comprise:
    determining that the first medication should not be delivered prior to completing the preparation of the second medication, wherein the notification comprises a message to wait for the preparation of the second medication to be completed before delivering the first medication, and comprises an estimated amount of time to complete the preparation of the second medication.

10. The system of claim 1, wherein the display device is a mobile device remote from the one or more processors, and assigned to an individual responsible for delivering the first medication or the second medication.

11. A method, comprising:
receiving, by a computing device, an identification of a first medication indicated for delivery to a first location within a healthcare facility, the identification of the first medication being received from a reader device and including information obtained from an active identification device affixed to a container of the first medication, the active identification device configured to automatically transmit the information wirelessly to the reader device when within a proximity of the reader device without a further action taken by a participant;
identifying, by the computing device, a preparation status of a second medication designated for delivery to a second location within the healthcare facility;
determining, by the computing device, delivery times and priorities for the first medication and the second medication, and a completion time for the second medication;
determining, based on the delivery times and priorities for the first medication and the second medication and the completion time for the second medication, whether the second medication should be delivered prior to delivering the first medication; and
providing, for display at a display device, when determining that the second medication should be delivered prior to delivering the first medication, a notification indicating the second medication should be delivered before delivering the first medication.

12. The method of claim 11, further comprising:
determining that the first medication should not be delivered prior to completing a preparation of the second medication;
providing, a notification to wait for the preparation of the second medication before delivering the first medication;
providing a prompt to request that the second medication be provided to a delivery pickup area for delivery prior to the delivery of the first medication; and
receiving, prior to the delivery of the first medication, from the display device, confirmation that the second medication was provided to the delivery pickup area for delivery to the second location prior to the delivery of the first medication to the first location.

13. The method of claim 12, further comprising:
receiving, based on a scanning of a container of the first medication, a second indication that a delivery person has received the first medication at the delivery pickup area for delivery to the first location;
wherein determining whether the second medication should be delivered prior to delivering the first medication is performed responsive to receiving the second indication.

14. The method of claim 11, further comprising:
determining that the second medication is a high priority medication, wherein determining that the first medication should not be delivered prior to delivering the second medication is based on the second medication being determined to be the high priority medication.

15. The method of claim 11, further comprising:
receiving, based on a scanning of a container of the second medication, progress information regarding the delivery of the second medication to the second location;
receiving a request to retrieve the progress information from a user; and
providing, responsive to the request, the progress information together with a last-known location of the second medication.

16. The system of claim 5, wherein the last-known location is not the second location.

17. The method of claim 11, further comprising:
providing, for display at the display device, a user interface comprising a prioritized list of medication orders, a first order in the prioritized list comprising the first medication;
selectively reordering the prioritized list of the user interface to display a second order for the second medication over the first order based on respective priorities associated with each of the medication orders in the prioritized list, respective due times associated with each of the medication orders, and respective patient locations associated with each of the medication orders.

18. The method of claim 11, wherein a preparation of the first medication is completed before a preparation of the second medication, the method further comprising:
determining an expiration time of the first medication or the second medication, wherein determining that the second medication should be delivered prior to delivering the first medication is further based on the expiration time of the first medication or the second medication.

19. The method of claim 18, further comprising:
determining that the first medication should not be delivered prior to completing the preparation of the second medication, wherein the notification comprises a message to wait for the preparation of the second medication to be completed before delivering the first medication, and comprises an estimated amount of time to complete the preparation of the second medication.

20. A non-transitory machine readable memory device storing instructions thereon that, when executed, cause a first computing device to perform operations comprising:
receiving an identification of a first medication indicated for delivery to a first location within a healthcare facility, the identification of the first medication being received from a reader device and including information obtained from an active identification device affixed to a container of the first medication, the active identification device configured to automatically transmit the information wirelessly to the reader device when within a proximity of the reader device without a further action taken by a participant;
identifying a preparation status of a second medication designated for delivery to a second location within the healthcare facility;
determining delivery times and priorities for the first medication and the second medication, and a completion time for the second medication;
determining, based on the delivery times and priorities for the first medication and the second medication and the completion time for the second medication, whether the second medication should be delivered prior to delivering the first medication; and
providing, for display at a display device, when determining that the second medication should be delivered prior to delivering the first medication, a notification indicating the second medication should be delivered before delivering the first medication.

\* \* \* \* \*